United States Patent
Kim et al.

(10) Patent No.: US 9,821,044 B2
(45) Date of Patent: Nov. 21, 2017

(54) CD4 T CELL VACCINE AND USE THEREOF

(71) Applicant: THE CATHOLIC UNIVERSITY OF KOREA INDUSTRYACADEMIC COOPERATION FOUNDATION, Seoul (KR)

(72) Inventors: Tai Gyu Kim, Seoul (KR); Hyun Il Cho, Gyeonggi-do (KR); Hye Mi Park, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/535,940

(22) Filed: Nov. 7, 2014

(65) Prior Publication Data

US 2016/0136251 A1 May 19, 2016

(30) Foreign Application Priority Data

Mar. 6, 2014 (KR) .................... 10-2014-0026476

(51) Int. Cl.
*C12N 5/10* (2006.01)
*A61K 48/00* (2006.01)
*A61K 39/00* (2006.01)

(52) U.S. Cl.
CPC .. *A61K 39/0011* (2013.01); *A61K 2039/5156* (2013.01); *A61K 2039/5158* (2013.01)

(58) Field of Classification Search
None
See application file for complete search history.

(56) References Cited

U.S. PATENT DOCUMENTS

2004/0219161 A1* 11/2004 Scholler ............. A61K 39/0011
 424/185.1
2012/0309091 A1* 12/2012 Ando ................. C07K 14/4703
 435/455

OTHER PUBLICATIONS

Guinn, et al. 4-1BBL cooperates with B7-1 and B7-2 in converting a B cell lymphoma cell line into a long-lasting antitumor vaccine. J. Immunol. 1999; 162: 5003-5010.*
Melero et al. Amplification of tumor immunity by gene transfer of the co-stimulatory 4-1BB ligand: synergy with the CD28 co-stimulatory pathway. Eur J Immunol. 1998; 28: 1116-1121.*
Jun Tang et al., "A novel self-assembled nanoparticle vaccine with HIV-1 Tat 49-57/HPV16E7 49-57 fusion peptide and GM-CSF DNA elicits potent and prolonged CD8+T cell-dependent anti-tumor immunity in mice", Vaccine 30:1071-1082, (2012).
Hyn-II Cho et al., "Design of immunogenic and effective multi-epitope DNA vaccines for melanoma" Cancer Immunol Immunother.61(3): 343-351, (Mar. 2012).
Petra Krause et al., "Prostaglandin E2 enhances T-cell proliferation by inducing the costimulatory molecules OX40L, CD70, and 4-1BBL on dendritic cells." Blood 113 (11): 2451-2460, 2009.
GenBank Accession No. GQ258349.1 GI:254575546, Cloning vector pRama-34, complete sequence.
Hye-Mi Park et al., "Alternative Cellular Cancer Vaccine Using Expanded CD4+T Cells", The 2013 Fall Conference of the Korean Association of Immunologists, (Nov. 7, 2013).
Hye-Mi Park et al., "Alternative Cellular Cancer Vaccine Using Expanded CD4+T Cells", 2nd Graduate school Conference of Department of Microbiology and Immunology, College of Medicine, (Dec. 4, 2013).

* cited by examiner

*Primary Examiner* — Ilia Ouspenski
(74) *Attorney, Agent, or Firm* — Lathrop Gage LLP

(57) ABSTRACT

The present invention relates to a CD4 T cell vaccine and a use thereof, and provides a CD4 T cell vaccine which can increase intracellular viability and effectively induce an antigen-specific cytotoxic T lymphocyte (CTL) response.

12 Claims, 8 Drawing Sheets

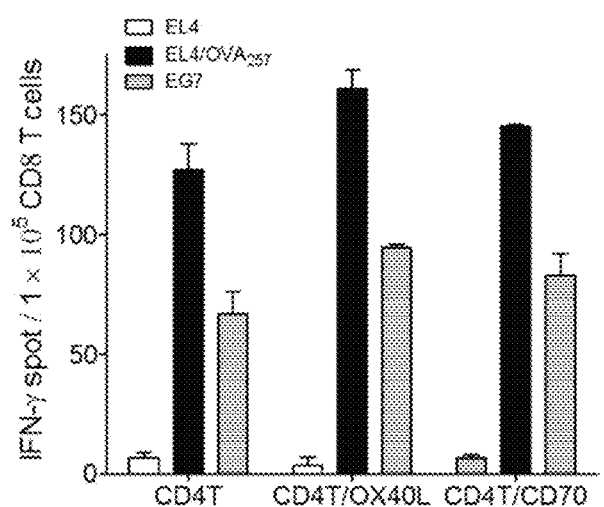
[FIG. 7]

```
                        SEQUENCE LISTING

<160> NUMBER OF SEQ ID NOS: 12

<210> SEQ ID NO 1
<211> LENGTH: 921
<212> TYPE: DNA
<213> ORGANISM: Mus musculus

<400> SEQUENCE: 1
atggcttgca attgtcagtt gatgcaggat acaccactcc tcaagtttcc atgtccaagg     60
ctcattcttc tctttgtgct gctgattcgt ctttcacaag tgtcttcaga tgttgatgaa    120
caactgtcca agtcagtgaa agataaggta ttgctgcctt gccgttacaa ctctcctcat    180
gaagatgagt ctgaagaccg aatctactgg caaaaacatg acaaagtggt gctgtctgtc    240
attgctggga aactaaaagt gtggcccgag tataagaacc ggactttata tgacaacact    300
acctactctc ttatcatcct gggcctggtc ctttcagacc ggggcacata cagctgtgtc    360
gttcaaaaga aggaagagg aacgtatgaa gttaaacact tggctttagt aaagttgtcc    420
atcaaagctg acttctctac ccccaacata actgagtctg gaaacccatc tgcagacact    480
aaaaggatta cctgctttgc ttccgggggt ttcccaaagc ctcgcttctc ttggttggaa    540
aatggaagag aattacctgg catcaatacg acaatttccc aggatcctga atctgaattg    600
tacaccatta gtagccaact agatttcaat acgactcgca accacaccat taagtgtctc    660
attaaatatg gagatgctca cgtgtcagag gacttcacct gggaaaaacc cccagaagac    720
cctcctgata gcaagaacac acttgtgctc tttggggcag gattcggcgc agtaataaca    780
gtcgtcgtca tcgttgtcat catcaaatgc ttctgtaagc acagaagctg tttcagaaga    840
```

```
aatgaggcaa gcagagaaac aaacaacagc cttaccttcg ggcctgaaga agcattagct    900
gaacagaccg tcttcccttta g                                            921

<210> SEQ ID NO 2
<211> LENGTH: 930
<212> TYPE: DNA
<213> ORGANISM: Mus musculus

<400> SEQUENCE: 2
atggaccagc acacacttga tgtggaggat accgcggatg ccagacatcc agcaggtact     60
tcgtgcccct cggatgcggc gctcctcaga gataccgggc cctcgcggga cgctgcgctc    120
ctctcagata ctgtgcgccc cacaaatgcc gcgctcccca cggatgctgc ctaccctgcg    180
gttaatgttc gggatcgcga ggccgcgtgg ccgcctgcac tgaacttctg ttcccgccac    240
ccaaagctct atggcctagt cgcttttggtt ttgctgcttc tgatcgccgc ctgtgttcct    300
atcttcaccc gcaccgagcc tcggccagcg ctcacaatca ccacctcgcc caacctgggt    360
acccgagaga ataatgcaga ccaggtcacc cctgtttccc acattggctg ccccaacact    420
acacaacagg gctctcctgt gttcgccaag ctactggcta aaaaccaagc atcgttgtgc    480
aatacaactc tgaactggca cagccaagat ggagctggga gctcatacct atctcaaggt    540
ctgaggtacg aagaagacaa aaaggagttg gtggtagaca gtcccgggct ctactacgta    600
tttttggaac tgaagctcag tccaacattc acaaacacag ccacaaggt gcagggctgg    660 gtctctcttg tttttgcaagc aaagcctcag gtagatgact tgacaacctt ggccctgaca    720
gtggaactgt tcccttgctc catggagaac aagttagtgg accgttcctg gagtcaactg    780
ttgctcctga aggctggcca ccgcctcagt gtgggtctga gggcttatct gcatggagcc    840
caggatgcat acagagactg ggagctgtct tatcccaaca ccaccagctt tggactcttt    900
cttgtgaaac ccgacaaccc atgggaatga                                    930

<210> SEQ ID NO 3
<211> LENGTH: 591
<212> TYPE: DNA
<213> ORGANISM: Mus musculus

<400> SEQUENCE: 3
atgattccgg aggaaggtcg cccttgcccc tgggttcgct ggagcgggac cgcgttccag     60
cgccaatggc catggctgct gctggtggtg tttattactg tgttttgctg ttggtttcat    120
tgtagcggac tactcagtaa gcagcaacag aggctgctgg agcaccctga ccgcacaca    180 gctgagttac agctgaatct cacagttcct cggaaggacc ccacactgcg ctggggagca    240
ggcccagcct tgggaaggtc cttcacacac ggaccagagc tggaggaggg ccatctgcgt    300
atccatcaag atggcctcta caggctgcat atccaggtga cactggccaa ctgctcttcc    360
ccaggcagca ccctgcagca cagggccacc ctggctgtgg gcatctgctc ccccgctgcg    420
cacggcatca gcttgctgcg tgggcgcttt ggacaggact gtacagtggc attacagcgc    480
ctgacatacc tggtccacgg agatgtcctc tgtaccaacc tcaccctgcc tctgctgccg    540
tcccgcaacg ctgatgagac ccttctttgga gttcagtgga tatgcccttg a            591

<210> SEQ ID NO 4
<211> LENGTH: 597
<212> TYPE: DNA
<213> ORGANISM: Mus musculus

<400> SEQUENCE: 4
```

-continued

```
atggaagggg aagggttca acccctggat gagaatctgg aaaacggatc aaggccaaga      60
ttcaagtgga agaagacgct aaggctggtg gtctctggga tcaagggagc agggatgctt    120
ctgtgcttca tctatgtctg cctgcaactc tcttcctctc cggcaaagga ccctccaatc    180
caaagactca gaggagcagt taccagatgt gaggatgggc aactattcat cagctcatac    240
aagaatgagt atcaaactat ggaggtgcag aacaattcgg ttgtcatcaa gtgcgatggg    300
ctttatatca tctacctgaa gggctccttt ttccaggagg tcaagattga ccttcatttc    360
cgggaggatc ataatcccat ctctattcca atgctgaacg atggtcgaag gattgtcttc    420
actgtggtgg cctcttttgg ctttcaaagat aaagtttacc tgactgtaaa tgctcctgat    480
actctctgcg aacacctcca gataaatgat ggggagctga ttgttgtcca gctaacgcct    540
ggatactgtg ctcctgaagg atcttaccac agcactgtga accaagtacc actgtga      597
```

<210> SEQ ID NO 5
<211> LENGTH: 8
<212> TYPE: PRT
<213> ORGANISM: Artificial Sequence
<220> FEATURE:
<223> OTHER INFORMATION: Ova257

<400> SEQUENCE: 5

Ser Ile Ile Asn Phe Glu Lys Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Trp1455

<400> SEQUENCE: 6

Thr Ala Pro Asp Asn Leu Gly Tyr Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Trp2180

<400> SEQUENCE: 7

Ser Val Tyr Asp Phe Phe Val Trp Leu
1               5

<210> SEQ ID NO 8
<211> LENGTH: 9
<212> TYPE: PRT
<213> ORGANISM: Artificial Sequence
<220> FEATURE:
<223> OTHER INFORMATION: gp10025

<400> SEQUENCE: 8

Glu Gly Ser Arg Asn Gln Asp Trp Leu
1               5

<210> SEQ ID NO 9
<211> LENGTH: 9
<212> TYPE: PRT
<213> ORGANISM: Artificial Sequence
<220> FEATURE:

```
<223> OTHER INFORMATION: MAGE 1 nonapeptide

<400> SEQUENCE: 9

Glu Ala Asp Pro Thr Gly His Ser Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: MART-APL peptide

<400> SEQUENCE: 10

Leu Ala Gly Ile Gly Ile Leu Thr Val
1               5

<210> SEQ ID NO 11
<211> LENGTH: 9
<212> TYPE: PRT
<213> ORGANISM: Artificial Sequence
<220> FEATURE:
<223> OTHER INFORMATION: naturally presented Melan?A/MART?1 nonamer
      peptide

<400> SEQUENCE: 11

Ala Ala Gly Ile Gly Ile Leu Thr Val
1               5

<210> SEQ ID NO 12
<211> LENGTH: 10
<212> TYPE: PRT
<213> ORGANISM: Artificial Sequence
<220> FEATURE:
<223> OTHER INFORMATION: PSA-1 peptide

<400> SEQUENCE: 12

Phe Leu Thr Pro Lys Lys Leu Gln Cys Val
1               5                   10
```

CD4 T CELL VACCINE AND USE THEREOF

CROSS-REFERENCE TO RELATED APPLICATIONS

This application claims the benefit of, and priority to, Korean Patent Application No. 1020140026476, filed on Mar. 6, 2014, the contents of which are incorporated herein by reference in its entirety.

BACKGROUND

1. Field of the Invention

The present invention relates to a CD4T cell vaccine which can induce an antigen-specific cytotoxic T lymphocyte (CTL) response, and a use thereof.

2. Discussion of Related Art

Studies on cancer immunotherapy have been focused on activation of both congenital immunity and adoptive immunity, particularly, on an anticancer T cell response of recognizing a target cell and, on some occasions, eliminating the target cell to prevent, regulate, and treat several kinds of infections and malignant diseases. A cytotoxic CD8T cell is a major immune system effector capable of recognizing and destroying a tumor cell through numerous cell killing mechanisms. Activation of the CD8 T cell requires involvement of a T cell receptor and an allogeneic peptide major histocompatibility complex (pMHC) class I and also a costimulatory signal. The tumor cell seems to express a MHC molecule and a costimulatory ligand at an insufficient level, and, thus, it is necessary to manipulate a cellular adjuvant such as a dendritic cell in order to induce or increase an appropriate tumor-reactive CD8T cell response.

The dendritic cell (DC) is a very effective and specialized antigen-presenting cell since it can express a MHC molecule and a costimulatory ligand at a high level. A dendritic cell loaded with a tumor-associated antigen for clinical application has already been studied; DC-based cell vaccines are the choice important in the current cancer immunotherapy strategies against various tumors. In spite of their high efficiency in causing an antigen-specific T cell response in vivo, the DC has a serious shortcoming as a cellular adjuvant since it is present in a human peripheral blood cell at a low ratio (0.1 to 0.5%) and it is necessarily difficult to obtain DC sufficient for clinical application. In order to identify a reliable source for an autologous APC (Antigen-Presenting Cell) as an alternative to the DC for immunotherapy, some researchers studied other autologous cells which can be obtained from a small amount of peripheral blood since it is possible to easily proliferate and obtain pure allogeneic groups. The other researchers and the inventors of the present invention exhibited that B cells activated in vitro by treatment with inflammatory cytokine, CD40L, and toll-like receptor ligands can induce effective T cell priming and therapeutic anti-tumor immunity in vivo. According to another report, an activated human γδ T cell exhibits an effective antigen-presenting activity similar to DC activity that promotes proliferation and differentiation of a naive T cell. A CD4 T cell also induced a functional memory CD8 T cell response. According to the prior report, direct cross-priming by peptide-loaded lymphocytes exhibited that a memory cytotoxic T cell response takes place in a mouse model. Another study demonstrated that a DC-stimulated CD4 T cell obtains pMHC-I and costimulatory CD80, CD40, OX40L and 4-1BBL from a bystander antigen-presenting DC, promotes a central memory CD8 T cell response and induces secretion of IL-2, and anti-tumor immunity mediated by CD40L and CD80 signal transduction. Further, a human CD4 T cell representing a viral epitope induces a functional virus-specific memory CD8 T cell response.

Nonetheless, a cell vaccine using a CD4 T cell which can directly stimulate a naive CD8 T cell similar to a natural APC in a tumor model has not been developed.

SUMMARY OF THE INVENTION

The present invention has been made in an effort to provide a CD4 T cell vaccine that serves as an antigen-presenting cell by overexpressing a transfected foreign antigen and a costimulatory ligand and increasing an antigen-specific cytotoxic T cell response.

The present invention has also been made in an effort to provide a pharmaceutical use using a therapeutic effect of an antigen-specific cytotoxic T cell response of the CD4 T cell vaccine.

An exemplary embodiment of the present invention provides a CD4 T cell vaccine which is transfected with nucleic acid encoding a foreign antigen; and nucleic acid encoding one or more costimulatory ligands selected from the group consisting of CD80, 4-1BBL, CD70, and OX40L.

Another exemplary embodiment of the present invention provides a method of treating tumors, pathogenic infectious diseases, or autoimmune diseases from a subject, including administering a pharmaceutically effective dose of the CD4 T cell vaccine of the present invention to the subject in need thereof.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which:

FIG. 1A illustrates a result obtained by culturing freshly isolated CD4 T cells using immune magnetic beads in a culture medium alone (-●-), in 5 μg/mL of αCD3 alone (-■-), in 5 μg/mL of αCD3 and 2 μg/mL of αCD28 (-▲-), and in αCD3/CD28-coated beads (-♦-) in the presence of 30 IU/mL of IL-2 (point: mean values of fold expansion over time; and bar: SD) and FIG. 1B illustrates an analysis result of surface molecule expression of CD4 T cells cultured with αCD3/CD28-coated beads for 7 days and freshly isolated CD4 T cells (shaded portion) included as a control;

FIG. 2A illustrates analysis results of expression of costimulatory molecules from cells obtained from respective groups of CD4 T cell expanded in vitro without RNA (Mock) and CD4 T cells RNA-transferred by electroporation in CD80 alone (CD80-T), in 4-1BBL alone (4-1BBL-T), and in CD80 and 4-1BBL(CD80/4-1BBL-T) with the lapse of 24 hours after electroporation, FIG. 2B illustrates proliferation results of OT-I cells in reactions with respect to expanded CD4 T cells obtained by labelling OT-I (CD45.2) cells with 5 μM CFSE and culturing them with CD80- and/or 4-1BBL-expressing CD4 T cells electroporated with Ova RNA and obtaining the cells on 3 days after culturing and analyzing the cells with a flow cytometry, and FIG. 2C illustrates analysis results of expression of costimulatory molecules from cells obtained from respective groups of CD4 T cells expanded in vitro and RNA-transfected by electroporation in CD70 alone (CD70-T) and OX40L alone (OX40L-T) with the lapse of 24 hours after electroporation;

FIG. 3A illustrates evaluation results of cell viability and apoptosis in the CD4 T cells transfected as illustrated in FIG. 2A, cultured in the presence of 30 IU/ml of IL-2 only, and stained with Annexin V and 7-AAD at 2 days after culturing, FIG. 3B illustrates the number of viable cells of the CD80- and/or 4-1BBL-expressing CD4 T cells transfected by electroporation as a result of a test for 5 days, and FIG. 3C illustrates that co-expression of CD80 and 4-1BBL in vivo extends maintenance of CD4 T cells as a result of administration of an RNA-transfected CD4 T cell to congenic (CD45.2) mice and measurement of the total number of cells (CD45.1) designed in spleens on days 2 and 5 after administration;

FIG. 4A illustrates a result of a test in which a CD80- and/or 4-1BBL-expressing CD4 T cell electroporated with Ova RNA is administered to mice intravenously 3 times at 4-day intervals, CD8 T cells are purified from pooled splenocytes on the eighth day after last immunization, an antigen-induced IFNγ is tested to EG7, $Ova_{257}$-pulsed EL4 cell (EL4/$Ova_{257}$) and un-pulsed EL4 cell (negative control) (the result illustrates the average number of spots from triplicate wells with SD (bars)), FIG. 4B illustrates a result of measurement of a ratio of $CFSE^{hi}$ and $CFSE^{low}$ target cells using CD45.1-positive cell gating with a flow cytometry, the $CFSE^{hi}$ and $CFSE^{low}$ target cells remaining after a 1:1 mixture of $Ova_{257}$-pulsed $CFSE^{hi}$ cells and $Ova_{257}$-un-pulsed$CFSE^{low}$-labelled splenocytes (CD45.1) is administered to the vaccinated mice described in FIG. 4A to measure in vivo cytotoxicity and the spleen is removed on the next day (a non-vaccinated (No Vax) mice are a negative control and a value in each panel represents a specific lysis ratio of $CFSE^{hi}$ to $CFSE^{low}$ target cells in the spleen), and FIG. 4C illustrates an analysis result of antigen-specific CD8 T cell proliferation through treatment of congenic (CD45.1) mice with a CFSE-labelled OT-I (CD45.2) cell on the day before immunization and CD45.2-positive cell gating on the second day after vaccination (the non-vaccinated (No Vax) mice are a negative control and values represent the percentage of expanded cells in the respective groups);

FIG. 5A illustrates a result obtained by subcutaneously inoculating $5×10^5$ liveEG7 cells to mice (4 mice per group) and 3 days later, vaccinating CD4 T cell vaccines including the CD4 T cell alone as described in FIG. 4A 3 times every 4 days, FIG. 5B exhibits a tumor growth in mice in which CD80/4-1BBL-T cell-vaccinated CD4 T cell, CD8 T cell, and NK cell are decreased and in a EG7-bearing mice intraperitoneally administered while reducing an antibody on 1 day and/or 2 days before immunization without vaccination (No Vax) as a control, and FIG. 5C illustrates a result obtained by subcutaneously administering $1×10^6$ EG7 cells (in the opposite flank) of a tumor-free (tumor-rejecting) mice at the end of the experiment described in FIG. 5A and measuring a tumor size (a naive unvaccinated mice inoculated with the same number of EG7 cells is a control, and a tumor size is indicated by a tumor area in $mm^2$ and a point represents a mean for each group of mice and a bar represents SD);

FIG. 6A illustrates evaluation results of an antigen-specific CD8 T cell response by intravenously administering CD4 T cell vaccines to mice as illustrated in FIG. 4A but using ME7 RNA including three melanosomal CD8 T cell epitopes ($Trp1_{455}$/$Trp2_{180}$/$gp100_{25}$), and conducting EliSpot assay to B16 melanoma, peptide-pulsed EL4 cells (EL4/$Trp1_{455}$, EL4/$TrP2_{180}$, and EL4/gp100) and a un-pulsed EL4 cell (negative control) on 8 days after last immunization, FIG. 6B illustrates a therapeutic anti-tumor effect of CD4 T cell vaccines in disease setting obtained by subcutaneously inoculating $1×10^5$ live B16 melanoma cells to mice and administering a CD80- and/or 4-1BBL-expressing CD4 T cell as immunization in the same manner as illustrated in FIG. 5A except that ME7 RNA is electroporated into the cell, and a tumor size is indicated by a tumor area in $mm^2$ and a point represents a mean for each group of mice and a bar represents SD (*P<0.0001, p=0.0034, *p=0.0321: by 2-way ANOVA); and FIG. 7 illustrates an evaluation result of antigen-specific CD8 T cell response of a CD70- or OX40L-expressing CD4 T cell by EliSpot assay.

DETAILED DESCRIPTION OF EXEMPLARY EMBODIMENTS

Figure 1A:
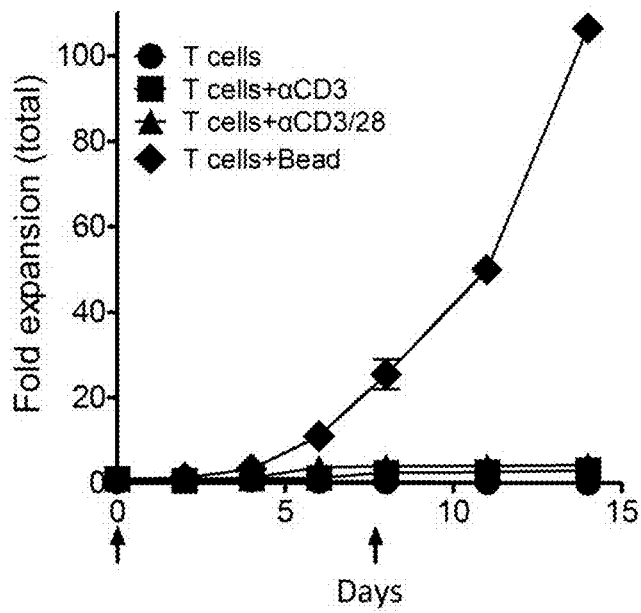
FIGS. 1A-1B illustrate expression results of costimulatory molecules in a naive CD4 T cell and a CD4 T cell proliferated in vitro.
Figure 1B:
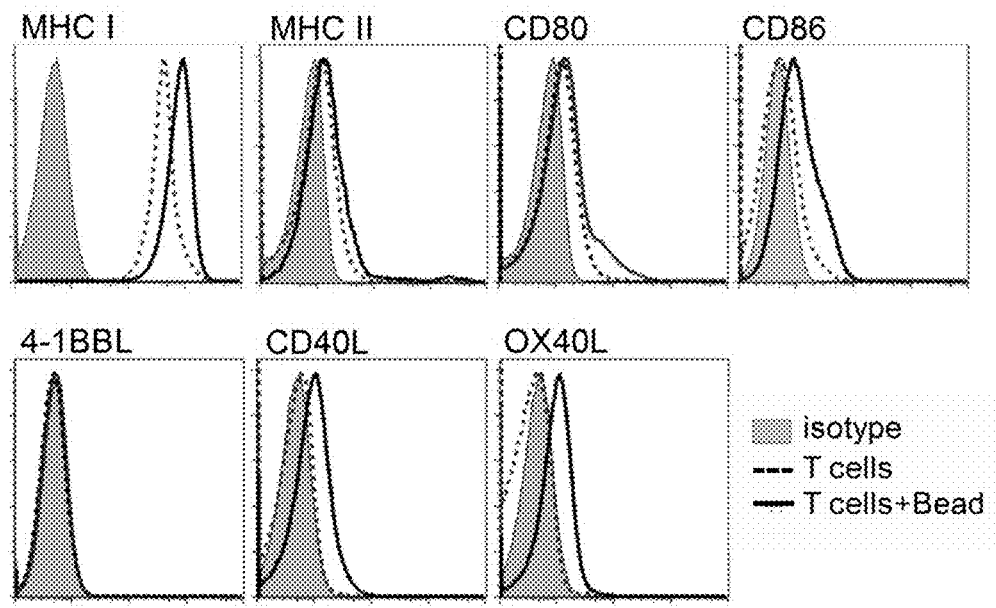

Hereinafter, the present invention will be described with reference to examples and comparative examples in detail. However, the present invention is not limited to these examples.

Hereinafter, a configuration of the present invention will be explained in detail.

The present invention relates to a CD4 T cell vaccine which is transfected with nucleic acid encoding a foreign antigen; and nucleic acid encoding one or more costimulatory ligands selected from the group consisting of CD80, 4-1BBL, CD70, and OX40L.

The present invention provides a CD4 T cell vaccine which can serve as an autologous antigen-presenting cell and induce an antigen-specific cytotoxic T cell response as an alternative to overcome the shortcoming of the conventional antigen-presenting cell, for example, dendritic cell, which is present in a small amount in a human peripheral blood cell and difficult to obtain in a large amount for clinical application.

In view of antigen-presenting activity, if the CD4 T cell vaccine is a CD4 T cell transfected with only nucleic acid encoding costimulatory ligands CD80 and 4-1BBL in a specific example, cell surface expression of the costimulatory ligands is increased as compared with a control and maintained for up to about 5 days. If nucleic acid encoding a foreign antigen is transfected to this CD4 T cell, antigen-specific CD8 T cell proliferation can be synergistically increased. Thus, it can be seen that the CD4 T cell can serve as an antigen-presenting cell.

In view of cellular vaccine, if the CD4 T cell vaccine is a cellular vaccine based on the conventional dendritic cell in a specific example, the CD4 T cell vaccine has a shortcoming of low intracellular viability while a CD8 T cell is stimulated in vivo, but it can be seen that the CD4 T cell transfected with CD80 and 4-1BBL can suppress spontaneous apoptosis and extend intracellular viability and thus can be used as an effective cellular vaccine. Therefore, it can have excellent efficacy as compared with the conventional cellular vaccines.

The CD4 T cell used in transfer of a foreign antigen and costimulatory ligands is a cell in an activation state stimulated in vitro and has no significant difference in expression level of CD80 and 4-1BBL from a resting CD4 T cell, but exhibits an increase in expression of OX40L.

The activation state of a T cell defines whether the T cell is "resting" (i.e., in the $G_0$ phase of the cell cycle) or "activated" after an appropriate stimulus such as the recognition of its specific antigen, or by stimulation with OKT3 antibody, PHA or PMA. The "phenotype" of the T cell (for example, naive, central memory, effector memory, lytic effectors, help effectors (TH1 and TH2 cells), and regulatory effectors) describes the function the cell exerts when activated. A healthy donor has T cells of each of these phenotypes, and which are predominately in the resting state. A naive T cell will proliferate upon activation, and then differentiate into a memory T cell or an effector T cell. It can then assume the resting state again, until it gets activated the next time, to exert its new function and may change its phenotype again. An effector T cell will be divided upon activation and antigen-specific effector function.

The stimulated CD4 T cell can be obtained by performing electroporation and transfer of an RNA encoding a foreign antigen and an RNA encoding costimulatory ligands to a CD4 T cell isolated from peripheral blood under IL-2 and a stimulated CD4 T cell mixed with αCD3/CD28-coated beads and cultured and proliferated, and mixing the CD4 T cells with the αCD3/CD28-coated beads at a ratio of the number of beads per unit cell of 1:1 to 2 and culturing and proliferating the mixture. The mixing ratio is adopted for relatively excellent proliferation, and according to a specific example of the present invention, when a resting CD4 T cell is cultured with αCD3 or a αCD3/CD28 mixture or αCD3/CD28-coated beads, the culture obtained from culturing with the αCD3/CD28-coated beads exhibits a 100 or more-fold increase in CD4 T cell proliferation.

Further, the stimulated CD4 T cell exhibits a significant increase in expression of other kinds of costimulatory ligands such as CD40L, OX40L, and CD86, and, thus, may affect proliferation, survival, and cytotoxic T cell response of a CD80- and 4-1BBL-transfected CD4 T cell. Preferably, it may affect an increasing aspect. For example, CD40L naturally proliferated in the stimulated CD4 T cell can induce an antigen-specific CD8 T cell and strong anti-tumor immunity in combination with other costimulatory ligands.

The term "antigen" is well understood in the art and includes any molecule that can bind to an antibody, as well as epitopes, peptides fragments of antigens which can bind to MHC molecules, and immunogens. In the present invention, an antigen may include, but is not limited to, a tumor antigen, a pathogen antigen, or an autoantibody (normal or disease-related).

Further, in the present specification, the term "foreign antigen" is used to mean that a molecule (antigen) which is naturally present or not in a cell is delivered into the cell from the outside. The delivery means transfection.

The tumor antigen is a tumor associated antigen (TAA) which refers to an antigen that is associated with a tumor. Examples of well-known TAAs include ovalalbumin, survivin, gp75, gp100, MDM2, MART-1, MAGE-1, MAGE-3, tyrosinase, telomerase, her-2/neu, α-1 fetoprotein, G250, NY-ESO-1, and the like. Further, sequences of some peptides fragments of the TAA which can bind to MHC molecules include $Ova_{257}$ (SIINFEKL: SEQ ID NO:5), tyrosinase-related protein $1_{455}$ ($Trp1_{455}$; TAPDNLGYA: SEQ ID NO:6), $Trp2_{180}$ (SVYDFFVWL: SEQ ID NO:7), and $gp100_{25}$ ($gp100_{25}$; EGSRNQDWL: SEQ ID NO:8), MAGE 1 nonapeptide (EADPTGHSY: SEQ ID NO:9), MART-APL peptide (LAGIGILTV: SEQ ID NO:10), naturally presented Melan-A/MART-1 nonamer peptide (AAGIGILTV: SEQ ID NO:11) or PSA-1 peptide (FLTPKKLQCV: SEQ ID NO:12), and the like. Additional sequences of the tumor associated peptides and antigens are known to those skilled in the art.

Examples of tumors associated with the tumor antigen include a solid tumor, a liquid tumor, a hematologic tumor, renal cell cancer, melanomas, breast cancer, prostate cancer, testicular cancer, bladder cancer, ovarian cancer, cervical cancer, stomach cancer, esophageal cancer, pancreatic cancer, lung cancer, neuroblastomas, glioblastomas, retinoblastomas, leukemias, myelomas, lymphomas, hepatoma, adenomas, sarcomas, carcinomas, blastomas, and the like.

The pathogen antigen refers to any disease causing organism or virus and also to attenuated derivatives thereof. The term "pathogen" refers to any virus or organism which is involved in the etiology of a disease and also to attenuated derivatives thereof. Such pathogens include, but are not limited to, bacteria, protozoan, fungal and viral pathogens such as *Helicobacter* sp., such as *Helicobacter pylori; Salmonella* sp.; *Shigella* sp.; *Enterobacter* sp.; *Campylobacter* sp.; various mycobacteria, such as *Mycobacterium leprae, Mycobacterium tuberculosis; Bacillus anthracis; Yersinia pestis; Francisella tularensis; Brucella* sp.; *Leptospira interrogans; Staphylococcus* sp., such as *S. aureus; Streptococcus* sp.; *Clostridum* sp.; *Candida albicans; Plasmodium* sp.; *Leishmania* sp.; *Trypanosoma* sp.; human immunodeficiency virus (HIV); hepatitis C virus (HCV); human papilloma virus (HPV); cytomegalovirus (CMV); HTLV; herpes virus, such as herpes simplex virus type 1, herpes simplex virus type 2, coronavirus, varicella-zoster virus, and Epstein-Barr virus; papilloma virus; influenza virus; hepatitis B virus; poliomyelitis virus; measles virus; mumps virus; or rubella virus.

The autoantibody includes, but is not limited to, an anti-nuclear antibody, an anti-γ-globulin antibody, an antibody to an autoblood component, or an antibody to an autoorgan. If the autoantibody is used as a foreign antigen, the CD4 T cell vaccine can induce strong anti-tumor immunity, and, thus, it can be effective in overcoming potential immunological tolerance to a self-antigen expressed in a normal tissue.

The term "costimulatory ligand" refers to a molecule involved in the interaction between receptor-ligand pairs expressed on the surface of antigen-presenting cells and T cells. Resting T cells require two or more signals for induction of cytokine gene expression and proliferation. One signal, the one that confers specificity, can be produced by the interaction between the MHC/peptide complex and the TCR/CD3 complex. The second signal is not antigen specific and is called the "costimulatory" signal. This signal is known as an activity provided by bone-marrow-derived accessory cells such as macrophages and dendritic cells. Costimulatory ligands mediate costimulatory signal(s), which are necessary, under normal physiological conditions, to achieve full activation of naive T cells. The present invention amplifies such roles of CD80, 4-1BBL, CD70, OX40L, and the like.

In the present invention, a nucleic acid to be transferred to the CD4 T cell is RNA. The term "RNA" refers to polymeric forms of ribonucleotides of any length, wherein the ribonucleotides or ribonucleotide analogs are joined together by phosphodiester bonds. The term "RNA" includes, for example, single-stranded, double-stranded and triple helical molecules, primary transcripts, mRNA, tRNA, rRNA, in vitro transcripts, in vitro synthesized RNA, branched polyribonucleotides, isolated RNA of any sequence, and the like. mRNA refers to an RNA that can be translated in a cell. Such mRNAs are typically capped and have a ribosome binding site (Kozak sequence) and a translational initiation codon.

The RNA encoding a foreign antigen can be appropriately adopted depending on a kind of an antigen.

The CD4 T cell vaccine of the present invention can express one or more costimulatory ligands selected from the group consisting of CD80, 4-1BBL, CD70, and OX40L.

The costimulatory ligand can be transfected in the form of an encoding nucleic acid into the CD4 T cell vaccine.

Therefore, preferably, the CD80 may be a human- or mouse-derived nucleic acid, and may be, for example, a base sequence represented by SEQ ID NO: 1, but not particularly limited thereto.

The 4-1BBL may be a human- or mouse-derived nucleic acid, and may be, for example, a base sequence represented by SEQ ID NO: 2, but not particularly limited thereto.

The CD70 may be a human- or mouse-derived nucleic acid, and may be, for example, a base sequence represented by SEQ ID NO: 3, but not particularly limited thereto.

The OX40L may be a human- or mouse-derived nucleic acid, and may be, for example, a base sequence represented by SEQ ID NO: 4, but not particularly limited thereto.

The nucleic acid encoding costimulatory ligands may be in the form of RNA.

Therefore, preferably, the CD4 T cell vaccine of the present invention may be transfected with an RNA encoding a tumor antigen; and an RNA encoding CD80 and 4-1BBL.

The RNA can be generated by any method known in the art. For example, an expression cassette includes a promoter (T7 promoter, SP6 promoter, and the like) suitable for in vitro transcription. The mRNA may include 3'UTRs and/or 5'UTRs in order to increase mRNA stability and translational efficiency.

The CD4 T cell vaccine of the present invention can be generated by transferring a foreign antigen-encoding RNA and a costimulatory ligand-encoding RNA to a stimulated CD4 T cell in an activated state, and a transfer method may employ electroporation with high efficiency and low toxicity or transfer by liposome.

For example, conditions for electroporation include field strength of 100 to 150 Volts/mm gap width (for example, 400 to 600 V over a 4 mm gap) for 2 to 10 ms using a square wave pulse, but can be appropriately adjusted by those skilled in the art.

The CD4 T cell vaccine transfected with a foreign antigen and a costimulatory ligand increases an antigen-specific T cell response, and, thus, exhibits excellent efficacy and can be used in treating tumors, pathogenic infectious diseases, or autoimmune diseases.

Therefore, the present invention provides a pharmaceutical composition including the CD4 T cell vaccine for treating tumors, pathogenic infectious diseases, or autoimmune diseases.

The tumors may include tumors associated with the above-described tumor antigen. Examples of the tumors may include a solid tumor, a liquid tumor, a hematologic tumor, renal cell cancer, melanomas, breast cancer, prostate cancer, testicular cancer, bladder cancer, ovarian cancer, cervical cancer, stomach cancer, esophageal cancer, pancreatic cancer, lung cancer, neuroblastomas, glioblastomas, retinoblastomas, leukemias, myelomas, lymphomas, hepatoma, adenomas, sarcomas, carcinomas, blastomas, and the like.

The pathogenic infectious diseases may include infectious diseases associated with the above-described pathogen antigen. Examples of the pathogenic infectious diseases may include gastritis, paratyphoid fever, food poisoning, meningitis, pneumonia, urinary tract infection, skin infection, bacteremia, tuberculosis, anthrax, plague, tularemia, leptospirosis, atopic dermatitis, septicemia, scarlatina, rheumatic fever, tetanus, candida vaginitis, malaria, black fever, human trypanosomiasis, AIDS, hepatitis C, cervical cancer, influenza, hepatitis B, poliomyelitis, mumps, measles, simple herpes, wart, or rubella.

The autoimmune diseases may include diseases associated with the above-described autoantibody. Examples of the autoimmune diseases may include systemic lupus erythematosus (SLE), rheumatoid arthritis (RA), rheumatoid fever, and the like, but are not particularly limited thereto.

The pharmaceutical composition may include an active agent with a pharmaceutically acceptable carrier, active or inert, making the composition suitable for diagnostic or therapeutic use in vitro, in vivo or ex vivo.

The term "pharmaceutically acceptable carrier" includes any of the pharmaceutical carriers compatible with T cells, such as a phosphate buffered saline solution, protein excipients including serum albumin such as human serum albumin (HSA), recombinant human albumin (rHA), gelatin, and casein. For examples of carriers, stabilizers and adjuvants, refer to Martin REMINGTON'S PHARM. SCI, 18$^{th}$ Ed. (Mack Publ. Co., Easton (1995)) and the "PHYSICIAN'S DESK REFERENCE", 58nd Ed., Medical Economics, Montvale, N.J. (2004). The term "carrier" may include a buffer or a pH adjusting agent. Typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (for example, cyclodextrins, such as 2-hydroxypropyl-quadrature-cyclodextrin), polyethylene glycols, antioxidants, antistatic agents, surfactants (for example, polysorbates such as "TWEEN 20" and "TWEEN 80"), lipids (for example, phospholipids, fatty acids), steroids (for example, cholesterol), and chelating agents (for example, EDTA). Agents for preventing or reducing ice formation may be included.

The pharmaceutical composition of the present invention can be prepared in various formulations as appropriate. Formulations suitable for parenteral administration, such as, for example, by intratumoral, intraarterial (in the joints), intravenous, intramuscular, intradermal, intraperitoneal, intranodal and subcutaneous routes, and carriers include antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous or intraperitoneal administration is the preferred method of administration for the CD4 T cell vaccine of the present invention. The dose of cells administered to a subject is in an effective amount, effective to achieve the desired beneficial therapeutic response in the subject over time, or to inhibit growth of cancer cells, or to inhibit infection. For example, the method can be practiced by obtaining and saving blood samples from the subject prior to infusion for subsequent analysis and comparison. Generally at least about $1\times10^4$ to $1\times10^6$ and typically, between $1\times10^8$ and $1\times10^{10}$ cells may be infused intravenously or intraperitoneally into a 70 kg patient over roughly 60 to 120 minutes. For administration, cells of the present invention can be administered at a rate determined by the LD-50 (or other measure of toxicity) of the cell type and the side-effects of the cell type at various concentrations in consideration of the mass and overall health of the subject. Administration can be accomplished via single or divided doses. The CD4 T cell vaccine of the present invention can supplement other treatments for a condition by known conventional therapy, including cytotoxic agents, nucleotide analogues and biologic response modifiers. Similarly, biological response modifiers are optionally added for treatment by the CD4 T cell vaccine of the present invention. For example, the CD4 T cell vaccine is optionally administered with an adjuvant, or cytokine such as GM-CSF, IL-12 or IL-2.

Yet another aspect of the present invention relates to a method of inducing or promoting an immune response to an antigen in a subject, particularly a patient with a tumor, a pathogenic infection disease, or an autoimmune disease. The method includes administering a pharmaceutically effective dose of the CD4 T cell vaccine to the patient in need thereof as described above.

Still another aspect of the present invention relates to the use of the CD4 T cell vaccine of the present invention for treating and/or preventing disease states. Examples of the diseases which can be treated by the method of the present invention may include the above-described tumors, pathogenic infectious diseases, and autoimmune diseases.

Therefore, still yet another aspect of the present invention provides a method of treating tumors, pathogenic infectious diseases, or autoimmune diseases from a subject by administering a pharmaceutically effective dose of the CD4 T cell vaccine to the subject in need thereof to enhance a tumor-, a pathogenic infectious disease-, or an autoimmune disease-specific immune response. Herein, administration of the CD4 T cell vaccine induces or promotes an immune response that inhibits, halts, delays, or prevents the onset or progression of disease states.

The subject may include human, dog, cat, mouse, and the like without limitation.

The "effective dose" means an amount necessary at least partly to attain the desired immune response or to delay or to entirely halt the onset or progression of a particular disease to be treated. The amount varies depending upon the health and physical condition of the individual to be treated, the racial background of the individual to be treated, the ability of the immune system of the individual that synthesizes an antibody, the degree of protection desired, the formulation of the vaccine, the assessment of the medical situation, and other relevant factors. It is expected that the amount will fall in a relatively broad range that can be determined through routine trials.

Hereinafter, the present invention will be explained in detail with reference to Examples. However, the following Examples are provided only for illustration but do not limit the contents of the present invention.

EXAMPLES

<Example 1> Experiment for Preparation of CD4 T Cell Expressing CD80, 4-1BBL, CD70, or OX40L as Costimulatory Ligand, and Pharmaceutical Use Thereof (Mice)

6-8-week-old female C57BL/6(B6) mice were purchased from Orient Bio (Seongnam, Korea) and B6.SJL (CD45.1) congenic and OT-I TCR transgenic mice were purchased from Jackson Laboratories (Bar Harbor, Me.), and were bred under pathogen-free condition in the animal laboratory of the Catholic University School of Medicine. Breeding and experiment on the animals was conducted according to the guidelines of the Institutional Animal Care and Use Committee.

(Cell Lines, Peptides and Antibodies)

EL4, Ovalbumin (Ova)-expressing EG7 and B16 melanoma cells were purchased from American Type Culture Collection (Manassas, Va.). Synthetic peptides representing CD8 T-cell epitope $Ova_{257}$ (SIINFEKL), tyrosinase-related protein $1_{455}$ ($Trp1_{455}$; TAPDNLGYA), $Trp2_{180}$ (SVYDFFVWL), and glycoprotein $100_{25}$ ($gp100_{25}$; EGSRNQDWL) with a purity of >80% were purchased from A&A Labs (San Diego, Calif.). Rat monoclonal antibodies against mouse CD3, CD28, NK, CD4, and CD8 were purchased from BioXCell (West lebanon, NH). Fluorescein-labelled antibodies for flow cytometry were purchased form eBioscience (San Diego, Calif.).

(Preparation of CD4 T Cell and RNA Electroporation)

CD4 T cells were purified using a MACS CD4 T cell isolation kit (Miltenyi Biotec GmbH, Germany) with a purity of >90%. For in vitro expansion, $4 \times 10^6$ CD4 T cells and αCD3/CD28-coated beads (Miltenyi Biotec) were mixed at a ratio of beads per unit cell of 1:1 (loaded Anti-Biotin MACSiBead particles per cell (bead-to-cell ratio)) and then incubated.

In an experiment, CD4 T cells were expanded in a plate coated with 5 μg/mL of αCD3 alone or together with 2 μg/mL of αCD28. 30 IU/mL of IL-2 was used in culturing cells.

For DNA templates, mouse CD80 and 4-1BBL were cloned to pcDNA3 vectors (Invitrogen, Carlsbad, Calif.). Antigen-specific immunity was evaluated using plasmid pcDNA3-Ova and pME7 encoding three melanosomal CD8 T cell epitopes, $Trp1_{455}$, $Trp2_{180}$, and $gp100_{25}$ (Cho & Celis, 2012). Further, in vitro transcription was carried out using the mMES SAGE mMACHINE kit (Ambion, Austin, Tex.). By applying a square-wave pulse (340 V, 2 ms) to in vitro proliferated CD4 T cells ($4 \times 10^6$) with an Electro-Porator device (TX830, BTX; San Diego, Calif.), a mixture including 20 μg of each RNA was transfected.

CD70 and OX40L were also transfected into CD4 T cells through the same process as described above, and $OVA_{257}$ peptide was selected as a foreign antigen and pulsed for 1 day.

1 day after culturing, an expression level of surface molecules on the CD4 T cells was measured. In the following experiments, these cells were used for vaccination.

(Assessment of In Vitro Apoptosis and In Vivo Cell Survival)

For in vitro apoptosis assay, after 2 days in culture in a presence of 30 IU/mL of IL-2, RNA-transfected CD4 T cells were stained with fluorescein-labelled annexin-V and 7-amino-actinomycin D (7-AAD) and analyzed by flow cytometry. Total cell counts were measured with trypan blue exclusion.

For in vivo cell survival assay, $5 \times 10^6$ RNAs-transfected CD4 T cells (CD45.1) were intravenously administered to a B6 wild-type mice. On days 2 and 5 post-injection, splenocytes were stained, and CD4- and CD45.1-positive cells were analyzed by flow cytometry.

(Immunization and Evaluation of Immune Response)

Mice were immunized intravenously with $5 \times 10^6$ CD4 T cells transfected with a mixture of RNAs to express CD80 and/or 4-1BBL and antigen (Ova or ME7). Mice received three booster immunizations every 4 days. To assess whether CD8 T cells were able to recognize antigen-specific targets including tumor cells, interferon-γ (IFNγ) enzyme-linked immunosorbent spot (EliSpot) assays were performed using freshly purified CD8 T cells from spleens. Responder CD8 T cells were incubated with peptide-pulsed or un-pulsed EL4 or with EG7 and B16 melanoma cells at various responder-to-stimulator cell ratios. Cultures were incubated at 37° C. for 20 h, and spots were developed as described by the EliSpot kit (BD Biosciences, Franklin Lakes, N.J.). Spot counting was done with an AID EliSpot Reader System (Strassberg, Germany).

OVA$_{257}$ peptide was pulsed to CD70 or OX40L RNA-transfected CD4 T cells for 1 day, and then, the immunization and immune response was evaluated through the same process as described above.

(In Vitro, In Vivo Proliferation and Cytotoxicity Assay)

OT-I cells (CD45.2) were labelled with carboxyfluorescein succinimidyl ester (CFSE; Molecular Probes, Eugene, Oreg.) at a final concentration of 5 μM at 37° C. for 15 minutes. For in vitro proliferation, 2×10$^5$ OT-I cells were seeded in a 96-well plate with 1×10$^5$ stimulator CD4 T cells (CD45.1) expressing CD80 and/or 4-1BBL. After 3 days in culture, the cells were stained with αCD8 (to allow gating for OT-I cells) and then analyzed. For in vivo proliferation, 2×10$^6$ CFSE-labelled OT-I cells were intravenously administered to a B6 congenic (CD45.1) mice. One day after cell infusion, mice were vaccinated with 5×10$^6$ CD80- and/or 4-1BBL-expressing CD4 T cells which were electroporated together with Ova RNA. On day 2 post-vaccination, splenocytes were stained in order to analyze CD8 T cells confined in a CD45.2-positive group.

In vivo cytotoxicity was measured as described in Tang et al, Vaccine 30: 1071-1082, 2012. In brief, splenocytes from congenic (CD45.1) mice, un-pulsed or pulsed with 10 μg/mL of Ova$_{257}$ peptide at 37° C. for 2 hours, were labelled with CFSE at a low concentration (0.5 μM; CFSE$^{low}$) and a high concentration (5 μM; CFSE$^{high}$) respectively. Both types of CFSE-labelled cells (2×10$^7$) were mixed equally in a 1:1 ratio and injected intravenously into immunized mice and high naive mice. Mice were euthanized 20 h later, and the ratio of CFSE$^{high}$ to CFSE$^{low}$ in splenocytes was determined.

(Evaluation of Therapeutic Antitumor Effect)

Mice received subcutaneous inoculations of 5×10$^5$ EG7 or 1×10$^5$ B16 tumor cells (per mouse) in a rear flank 3 days before their first immunization. In some instances, survivor mice (that had rejected tumors) were rechallenged with 1×10$^6$ EG7 cells in the opposite flank. For the depletion of lymphocyte subsets, each mouse received intraperitoneal administration of 300 μg of αNK, αCD4, or αCD8 on days −2 and/or −1 relative to immunization. Depletions were confirmed with blood samples using flow cytometry. Tumor growth was monitored every 3 to 4 days in individual tagged mice by measuring 2 opposing diameters with calipers. Results are presented as mean tumor size (area in mm$^2$)±SD for every treatment group at various time points until the termination of the experiment.

(Statistical Analysis)

The tumor sizes were analyzed for significance by 2-way ANOVA. All the analyses and graphs were done using Prism 5.01 software (GraphPad, San Diego, Calif.).

<Experimental Example 1> Limited Expression Experiment of Costimulatory Ligand on In Vitro Expanded CD4 T Cells To address the hypothesis that genetically engineered CD4 T cells expressing a costimulatory ligand at a high level can serve as natural APCs which induce cytotoxic CD8 T cells, the optimum in vitro conditions for expanding CD4 T cells and surface expression of molecules involved in antigen presentation and costimulation and interacting with CD8 T cells were investigated. Freshly isolated CD4 T cells were incubated in plates coated with either αCD3 alone or combination of αCD3 and αCD28, and together with commercial αCD3/CD28-coated beads, respectively, in the presence of low-dose IL-2. The expansion of CD4 T cells over 15 days was clearly higher (more than 100-fold) in a culture with the αCD3/CD28-coated beads (1:1 ratio to cells) versus those with other conditions and with IL-2 alone (p=0.0002; FIG. 1A). Further, it was observed that ratios of beads to cells of 1:1 and 2:1 are the most efficient, and were equivalent in stimulating CD4 T cells (data not shown).

Subsequently, these CD4 T cells stimulated with αCD3/CD28-coated beads for 7 days were examined for surface expression of MHC and costimulatory molecules. The number of cells expressing MHC class I, CD86, CD40L, and OX40L was higher in expanded CD4 T cells compared to freshly isolated CD4 T cells. Moreover, the levels of MHC class II and CD80 expression were slightly augmented in expanded CD4 T cells whereas 4-1BBL expression was unaffected. Hence, to improve natural APC function, we sought to express CD80 and 4-1BBL in expanded CD4 T cells, as these molecules are involved in complete T cell activation together with pMHC/TCR engagement.

Figure 2A:
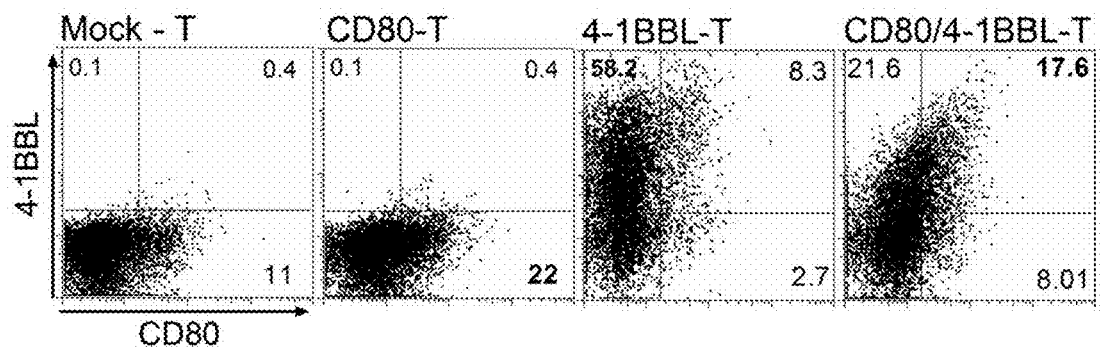
FIGS. 2A-2C illustrate confirmation results of expression of CD80 and 4-1BBL in CD4 T cells that expresses CD80- and/or 4-1BBL established by RNA transfer by electroporation.

<Experimental Example 2> Stimulatory Ability Test of CD4 T Cell Expressing CD80, 4-1BBL, CD70, and OX40L with Respect to Antigen-Specific T Cell In Vitro In order to enhance expression of CD80 and 4-1BBL, a single RNA or an RNA mixture encoding CD80 and/or 4-1BBL was electroporated in the in vitro expanded CD4 T cells. On the first day after electroporation, surface expression of the transfected cells (hereinafter, referred to as CD80-T, 4-1BBL-T, CD80/4-1BBL-T cells, CD70-T and OX40L-T cells) was analyzed. Phenotypic analysis of mock-electroporated CD4 T cells (mock-T cells) was shown for comparison (FIG. 2A).

In the RNA-transfected CD4 T cells, expression levels of CD80 and 4-1BBL on the cell surfaces were exhibited as positive proportion of each marker. The mock-T cells expressed 11.4% of CD80 and 0.5% of 4-1BBL, the CD80-T cells expressed 22.3% of CD80, the 4-1BBL-T cells expressed 66.5% of 4-1BBL, and the CD80/4-1BBL-T cells expressed 25.6% of CD80 and 39.2% of 4-1BBL. Thus, it could be confirmed that the expression levels were higher than those of the mock-electroporated cells. Expression of CD80 and 4-1BBL was maintained for 5 days after electroporation (data not shown).

In order to evaluate a costimulatory effect of CD80 and/or 4-1BBL in vitro and the APC function of expanded CD4 T cells, CFSE-labelled OT-I/CD45.2 cells were cultured together with CD80- and/or 4-1BBL-expressing CD4 T cells transfected with Ova RNA.

Figure 2B:
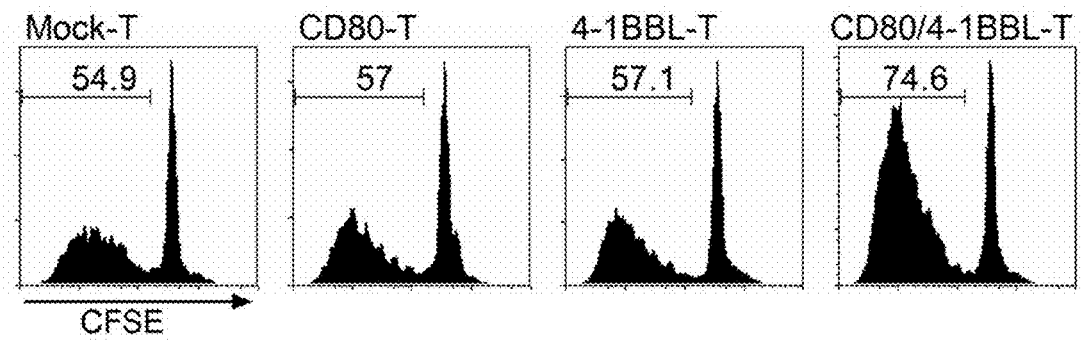

CD80-T and 4-1BBL-T cells induced moderate OT-I proliferative responses in comparison to mock-T cells (57% for the CD80-T cells, 57.1% for the 4-1BBL-T cells as compared with 54.9% for the mock-T cells), OT-I cells were proliferated at 74.6% when cultured with CD80/4-1BBL-T (FIG. 2B).

Figure 2C:
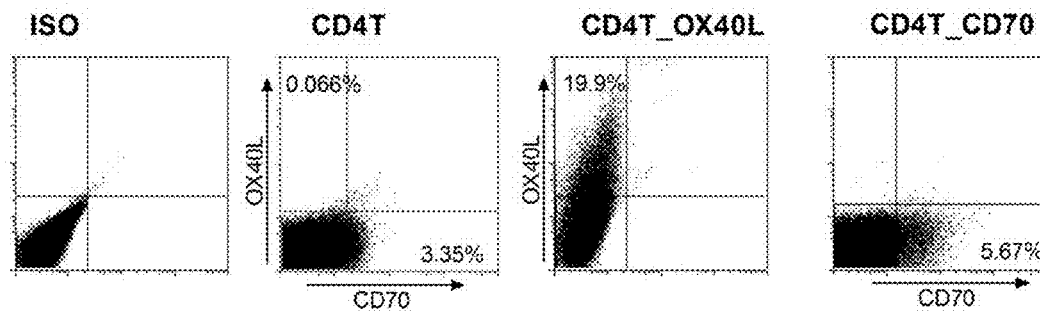

Further, as illustrated in FIG. 2C, the mock-T cells expressed 3.35% of CD70 and 0.0667% of OX40L, but the CD70-T cells expressed 5.67% of CD70, and the OX40L-T cells expressed 19.9% of OX40L. Thus, there was a remarkable increase in OX40L as compared with the mock-electroporated cells.

These results suggest that in vitro expanded CD4 T cells were able to play a role as natural APCs, and expression of CD80 and/or 4-1BBL, CD70, OX40L is beneficial to proliferation of CD8 T cells in vitro.

<Experimental Example 3> Viability Test of CD4 T Expressing CD80 and 4-1BBL

One of the obstacles facing cellular vaccination is the insufficient endurance of infused cells (as APCs) in vivo for the stimulation of CD8 T cells. In this respect, a survival rate of CD4 T cells transfected with CD80 and/or 4-1BBL was analyzed.

Figure 3A:
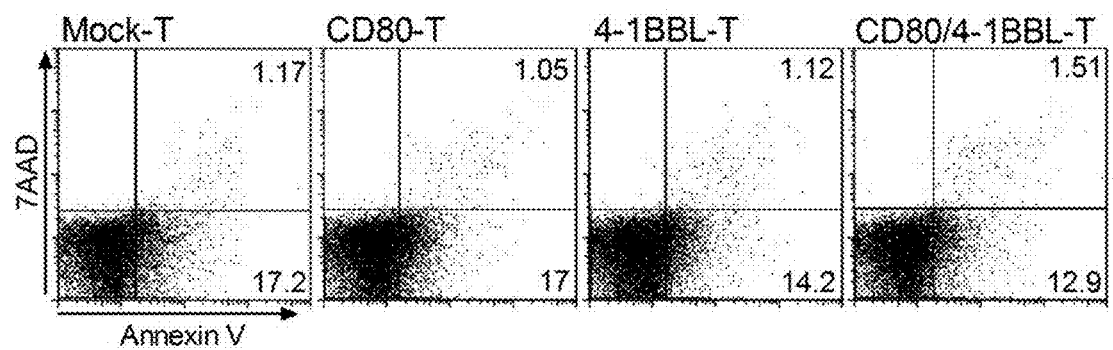
FIGS. 3A-3C illustrate that expression of CD80 and 4-1BBL in CD4 T cells increases cell vitality.

4-1BBL expression in CD4 T cells prevented impulsive cell death compared to mock- and CD80-transfected CD4 T cells (14.2% for the 4-1BBL-T cells as compared with 17.2% for the mock-T cells and 17.0% for the CD80-T cells), and expression of CD80 in addition to 4-1BBL enhanced this early cell survival benefit (12.9% for the CD80/4-1BBL-T) (FIG. 3A).

Likewise, live cell numbers of CD4 T cells transfected with CD80 and/or 4-1BBL in vitro for 5 days in the presence of low-dose t of IL-2 was tested.

Figure 3B:
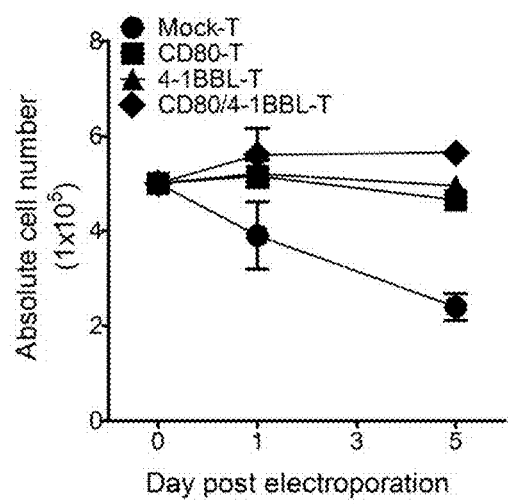

The live cell number of CD80/4-1BBL-T cells was slightly higher than that of the CD80 cells or 4-1BBL-T cells (FIG. 3B).

More interesting is that the number of the mock-T cells was decreased to be less than about two times the number of the CD80-T cells or 4-1BBL-T cells.

Figure 3C:
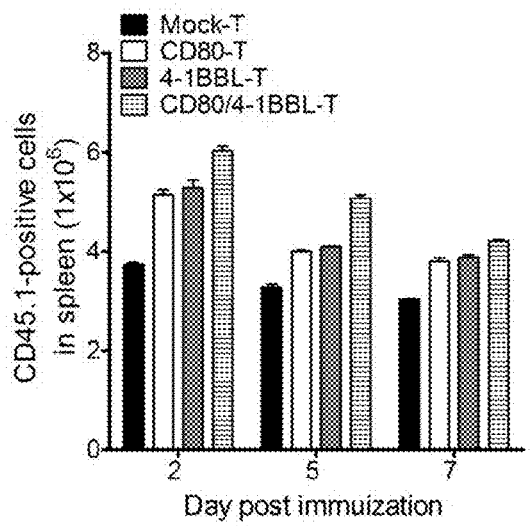

Further, in vivo vitality of genetically engineered CD4 T cells transfected with CD80 and/or 4-1BBL RNA was examined using CD45.2 congenic mice as a recipients (FIG. 3C). The splenocytes were obtained at various time points after cell infusion, and the absolute number of CD45.1-positive CD4 T cells in the spleen was enumerated. Similar to results from in vitro studies, the transfection of CD4 T cells with CD80 and/or 4-1BBL allowed their persistence in higher numbers in hosts, compared to Mock-T cells, and infusion with CD80/4-1BBL-T cells demonstrated significantly prolonged endurance in vivo. Taken together, these results indicate that CD4 T cells expressing CD80 and 4-1BBL showed enhanced in vitro cell vitality while inhibiting apoptosis, and that in vivo survival benefits can be achieved when CD80 and 4-1BBL are present together.

Figure 4A:
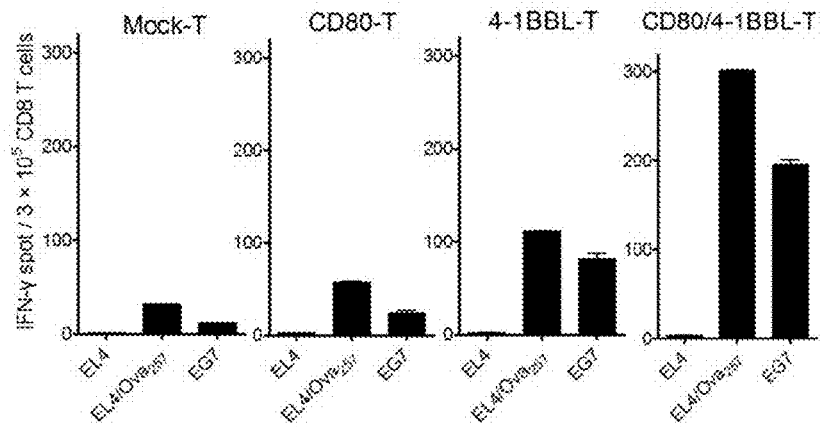
FIGS. 4A-4C exhibit immunogenicity of a CD80- and/or 4-1BBL-expressing CD4 T cell.

<Experimental Example 4> Test of Antigen-Specific CD8T Cell Activation and Proliferation by CD4 T Cell Whether genetically engineered CD4 T cells expressing CD80 and/or 4-1BBL can induce an antigen-specific CD8 T cell response was evaluated. The first focus was on whether inoculation of a CD4 T cell vaccine can generate an antigen-specific CD8 T cell in vivo. A CD4 T cell vaccine which is the same but electroporated with Ova RNA in various conditions was intravenously administered to a B6 mice three times. On the eighth day after last immunization, a functional activity of freshly isolated CD8 T cells (without additional stimuli) from the spleen was evaluated by EliSpot assay (FIG. 4A).

Antigen-specific recognition is a proof for a peptide-pulsed target (EL4 cell) and an ova-expressing EG7 tumor cell. In particular, in the case of a CD80/4-1BBL-T cell vaccination, the number of IFNγ spots was calculated significantly higher as compared with the case of other CD4 T cell vaccination (two times higher for the EG7 tumor cells as compared with the 4-BBL-T cells).

Figure 4B:
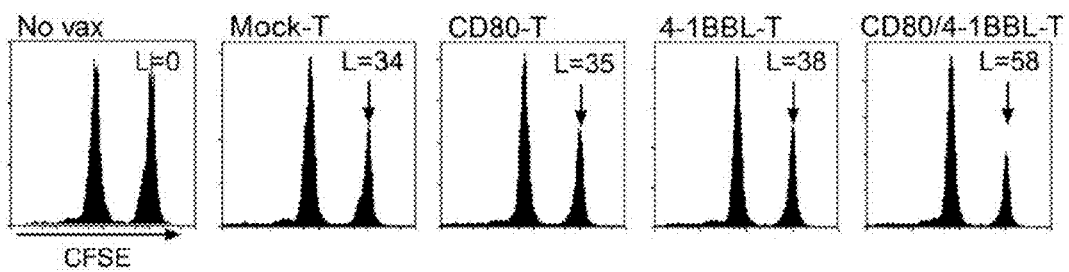

Further, in order to confirm the APC function of expanded CD4 T cells in vivo, CFSE-labelled OT-I/CD45.2 cells were infused into congenic CD45.1 mice, and a CD80- and/or 4-1BBL-expressing CD4 T cell was vaccinated in various conditions. Almost all of OT-I cells obtained from the non-vaccinated mice remained as being not divided, whereas the mice vaccinated with the CD80/4-1BBL-T cells exhibited excellent OT-I proliferative responses in vivo as compared with the other CD4 T cell-vaccinated mice (FIG. 4B).

Furthermore, effector cytolytic function of the antigen-specific CD8 T cells was evaluated with a target cell pulsed with $Ova_{257}$ peptide ($CFSE^{high}$) using the in vivo cytotoxicity assay as described above.

Figure 4C:
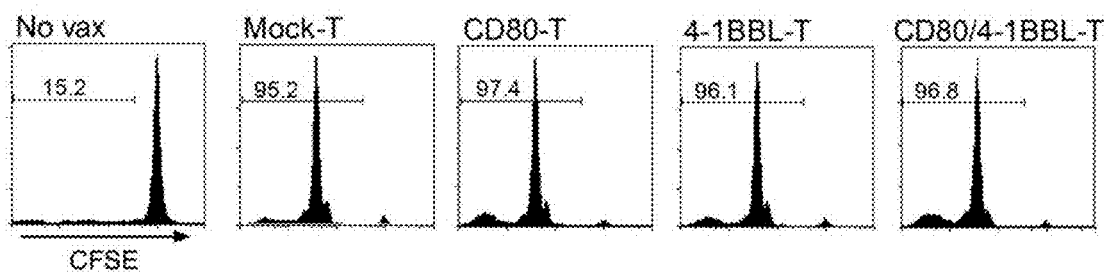

Mice vaccinated with the CD80/4-1BBL-T cell had a much higher level of the effector cytotoxic function as compared with CD8 T-cell response induced by another conditioned T cell vaccination (58% vs 34 to 38%; FIG. 4C).

As a whole, these results suggest that in vitro expanded CD4 T cells can process a foreign antigen into peptides and present pMHC-I on the cell surface so as to be supplied as a natural APC, and CD80 and 4-1BBL expression of the CD4 T cells increases such an APC function in vivo.

<Experimental Example 5> Efficacy Test of CD4 T Cell Expressing CD80 and 4-1BBL in EG7 Tumor Model Whether CD8 T cells generated by CD4 T cell vaccination have an in vivo therapeutic antitumor effect against established tumors was evaluated. An EG7 tumor was subcutaneously inoculated to mice. 3 days later, vaccination was initiated and provided three times at 4-day intervals.

Figure 5A:
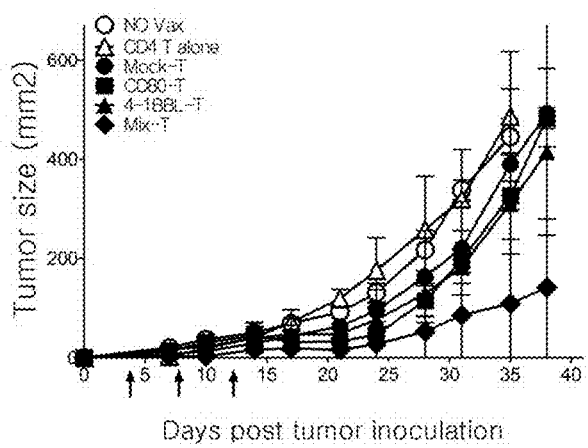
FIGS. 5A-5C exhibit a therapeutic anti-tumor effect of a CD80- and/or 4-1BBL-expressing CD4 T cell.

In the case of administration of CD4 T cells alone (without an antigen), a tumor growth rate was not decreased as compared with the non-vaccinated mice (FIG. 5A). The 4-1BBL-T cells had a considerably high antitumor effect (three of four mice exhibiting complete tumor rejection). On the contrary, vaccination with mock-T and CD80-T cells had negligible therapeutic effect.

Figure 5B:
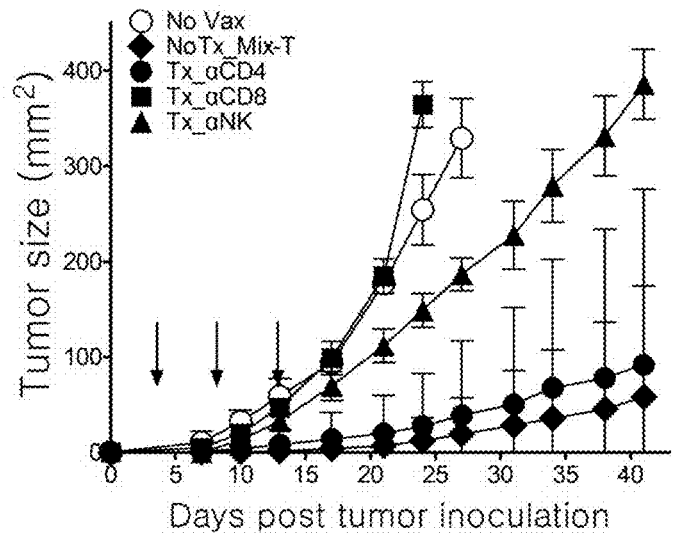

Further, the roles of NK cells and CD4 T cells that could participate in the induction of the CD8 T-cell response and/or synergize with CD8 T cells in fighting established tumors were evaluated (FIG. 5B).

A decrease in CD4 T cells had no significant deleterious effect on the therapeutic advantage of CD80/4-1BBL-T cell vaccination, but a decrease in CD8 T cells completely abolished the therapeutic antitumor effect, suggesting that the CD8 T cells are important for rejection against established tumors. A decrease in NK cells has a moderate effect on the therapeutic benefit, suggesting that these cells will somewhat contribute to inhibit the tumor growth.

Figure 5C:
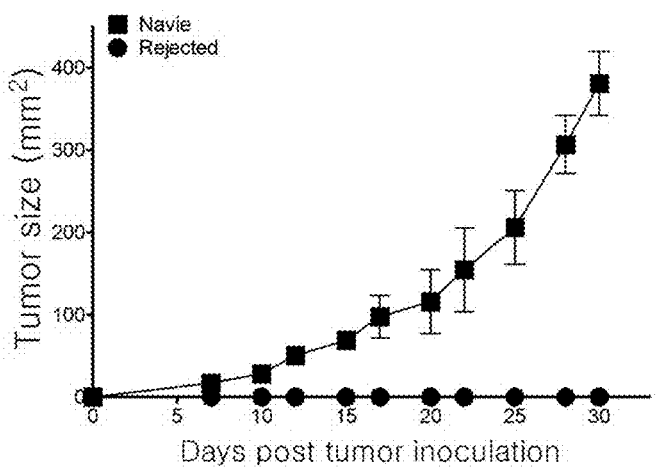

2 months after first vaccination, EG7 was subcutaneously rechallenged to the mice exhibiting tumor rejection to evaluate long-term immunity (FIG. 5C).

As compared with a naive control challenged with the same tumor, any one of the mice did not develop a tumor. Further, the mice exhibiting tumor rejection had a higher level of an antigen-specific CD8 T cell response (data not shown). This suggests that CD80/4-1BBL-T cell vaccination can induce an antigen-specific memory CD8 T cell response for a long time.

<Experimental Example 6> Efficacy Test of CD4 T Cell Expressing CD80 and 4-1BBL in B16 Melanoma Model In order to evaluate whether a CD8 T cell response induced by CD4 T cell vaccination exhibits an activity in disease setting, an in vivo antitumor effect was tested using plasmid ME7 including three CD8 T cell epitopes derived from melanosomal proteins Trp1, Trp2, and gp100 (Cho & Celis, *CII* 61, pp. 343 to 351, 2012).

Firstly, whether vaccination with ME7 RNA-transfected CD4 T cell induces self-antigen-specific CD8 T cells in vivo was evaluated. This is because these melanosomal proteins are also expressed by normal melanocytes. As described above, after the mice were immunized (inoculated three times every 4 days) with the CD4 T cells adjusted in various conditions, antigen-specific recognition of CD8 T cells was tested.

Figure 6A:
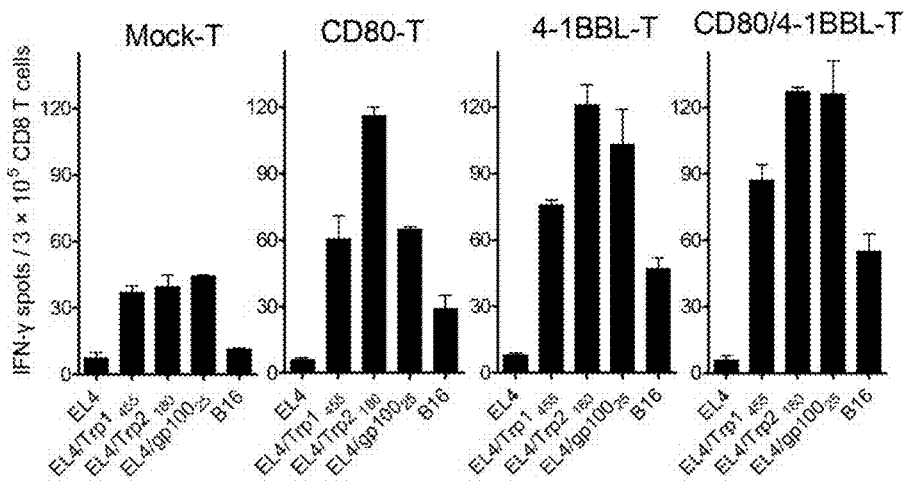
FIGS. 6A-6B exhibit a therapeutic anti-tumor effect of a CD80- and/or 4-1BBL-expressing CD4 T cells in a melanoma tumor model.
Figure 6B:
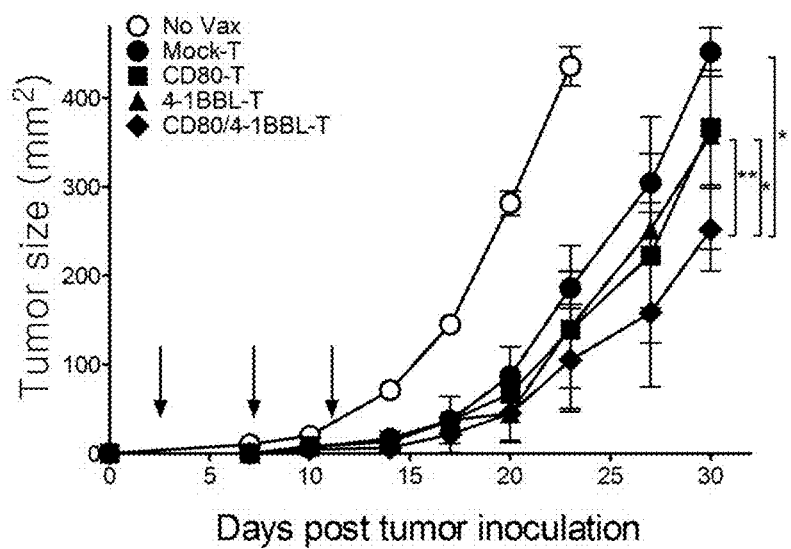

The mock-T cell vaccination generated a low immune repose, but as measured by EliSpot assay, all CD4 T cell vaccinations induced substantial CD8 T cell responses with respect to all of the three melanosomal epitopes. CD80/4-1BBL-T cell vaccination yielded significantly higher number of IFNγ spots than did other CD4 T cell vaccinations (FIGS. 6A-6B). More important is that the CD8 T cells obtained from CD4 T cell vaccinated mice effectively recognized not only a peptide-pulsed target but also a B16 melanoma cells.

Further, the in vivo antitumor effect of these CD4 T cell vaccines was examined. After subcutaneous inoculation of B16 melanomas, the mice were immunized with the CD4 T cells adjusted in various conditions according to the same protocol.

CD4 T cell vaccination delayed the tumor growth for about 1 week in such a very aggressive tumor model and exhibited a significant therapeutic benefit as compared with the non-vaccinated control (FIG. 6B).

The CD80/4-1BBL-T cells had a remarkably higher antitumor effect, but the CD80- and 4-1BBL-T cells had a moderate therapeutic advantage as compared with the mock-T cells. This suggests that vaccination with CD4 T cell expressing CD80 and 4-1BBL is effective in avoiding any potential tolerance against a self-antigen expressed in a normal tissue, and resultantly exhibits a significant antitumor therapeutic effect against established tumors.

Further, according to a result of evaluation on whether a genetically engineered cell expressing OX40L or CD70 can induce an antigen-specific cell response, as illustrated in FIG. 7, CD70-T cell and OX40L-T cell vaccination produced a significantly higher number of IFNγ spots as compared with vaccination with other CD4 T cell.

The present invention provided a CD4 T cell vaccine that extends intracellular viability and increases an antigen-specific cytotoxic T cell response.

The CD4 T cell vaccine can be used in treating tumors, pathogenic infectious diseases, or autoimmune diseases with excellent efficacy.

While the invention has been illustrated and described with reference to certain exemplary embodiments thereof, it will be understood by those skilled in the art that various changes in form and details may be made therein without departing from the spirit and scope of the invention as defined by the appended claims.

What is claimed is:

1. A CD4+ T cell vaccine, wherein the CD4+T cell is transfected with nucleic acid encoding a tumor antigen; and
  a nucleic acid encoding two or more costimulatory ligands selected from the group consisting of CD80, 4-1BBL, CD70, and OX40L,
  wherein a subject treated with the CD4+T cell vaccine generates a CD8+T cell immune response to the tumor antigen.

2. The CD4+ T cell vaccine of claim 1, wherein the tumor antigen is selected from the group consisting of ovalalbumin, survivin, gp75, gp100, MDM2, MART-1, MAGE-1, MAGE-3, tyrosinase, telomerase, her-2/neu, α-1 fetoprotein, G250, NY-ESO-1, Ova$_{257}$ (SEQ ID NO:5), tyrosinase-related protein 1$_{455}$ (Trp1$_{455}$; SEQ ID NO:6), Trp2$_{180}$ (SEQ ID NO:7), gp100$_{25}$(gp100$_{25}$; SEQ ID NO:8), MAGE 1 nonapeptide (SEQ ID NO:9), MART-APL peptide (SEQ ID NO:10), naturally presented Melan-A/MART-1 nonamer peptide (SEQ ID NO:11), and PSA-1 peptide (SEQ ID NO:12).

3. The CD4+ T cell vaccine of claim 1, wherein the CD80 comprises a nucleotide sequence comprising SEQ ID NO: 1.

4. The CD4+ T cell vaccine of claim 1, wherein the 4-1BBL comprises a nucleotide sequence comprising SEQ ID NO: 2.

5. The CD4+ T cell vaccine of claim 1, wherein the CD70 comprises a nucleotide sequence comprising SEQ ID NO: 3.

6. The CD4 T cell vaccine of claim 1, wherein the OX40L comprises a nucleotide sequence comprising SEQ ID NO: 4.

7. The CD4+ T cell vaccine of claim 1, wherein the CD4+ T cell is transfected with an RNA encoding the tumor antigen; and RNAs encoding CD80 and 4-1BBL.

8. The CD4+ T cell vaccine of claim 1, wherein the CD4+T cell vaccine is transfected with an RNA encoding the tumor antigen; and RNAs encoding CD70 and OX40L.

9. The CD4+ T cell vaccine of claim 1, wherein the CD4+ T cell is prepared by
  transducing an RNA encoding the tumor antigen and RNAs encoding the costimulatory ligands to a CD4+ T cell isolated from peripheral blood through electroporation, and
  culturing the transduced CD4+ T cells in the presence of IL-2 and αCD3/CD28-coated beads, wherein the ratio of αCD3/CD28-coated beads to CD4+ T cells is 1:1 to 1:2.

10. A method of treating tumors in a subject, the method comprising:
  administering a pharmaceutically effective dose of the CD4+T cell vaccine of claim 1 to the subject in need thereof.

11. The method of claim 10, wherein the tumors include any one of a solid tumor, a liquid tumor, a hematological tumor, renal cell cancer, melanomas, breast cancer, prostate cancer, testicular cancer, bladder cancer, ovarian cancer, cervical cancer, stomach cancer, esophageal cancer, pancreatic cancer, lung cancer, neuroblastomas, glioblastomas, retinoblastomas, leukemias, myelomas, lymphomas, hepatoma, adenomas, sarcomas, carcinomas, or blastomas.

12. The CD4+ T cell vaccine of claim 1, wherein the CD4+ T cell is transfected with CD80 and 4-1BBL.

* * * * *